(12) United States Patent
Bertoch et al.

(10) Patent No.: US 6,890,322 B2
(45) Date of Patent: May 10, 2005

(54) CATHETER SECURING DEVICE

(75) Inventors: Todd M. Bertoch, APO (AP); Ted F. Gingrich, San Antonio, TX (US); Steven C. Walker, Balwin, MO (US); John M. Shepherd, San Antonio, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 281 days.

(21) Appl. No.: 09/894,880

(22) Filed: Jun. 29, 2001

(65) Prior Publication Data

US 2002/0095119 A1 Jul. 18, 2002

Related U.S. Application Data

(60) Provisional application No. 60/214,745, filed on Jun. 29, 2000.

(51) Int. Cl.[7] .................................................. A61M 5/32
(52) U.S. Cl. ................................. 604/174; 128/DIG. 26
(58) Field of Search ................................. 604/177, 179; 128/200.27, 209.11, 209.12, 207, 14, 207.15, 207.17, 207.18, DIG. 6, 26, 861

(56) References Cited

U.S. PATENT DOCUMENTS

| | | | |
|---|---|---|---|
| 2,521,084 A | 9/1949 | Oberto | 128/141 |
| 2,669,988 A | 2/1954 | Carpenter | 128/136 |
| 2,693,182 A | 11/1954 | Phillips | |
| 2,820,457 A | 1/1958 | Phillips | |
| 2,882,893 A | 4/1959 | Godfroy | 128/136 |
| 2,908,269 A | 10/1959 | Cheng | |
| 3,467,427 A | 3/1968 | Moberg | 292/322 |
| 3,602,227 A | 8/1971 | Andrew | |
| 3,760,811 A | 9/1973 | Andrew | |
| 3,774,616 A | 11/1973 | White et al. | |
| 3,908,665 A | 9/1975 | Moses | 128/351 |
| 4,112,936 A | 9/1978 | Blachly | 128/136 |
| 4,183,119 A | 1/1980 | Stewart et al. | 24/16 PB |
| 4,198,970 A | 4/1980 | Luomanen | 128/207.15 |
| 4,205,819 A | 6/1980 | Soika | |
| 4,222,391 A | 9/1980 | Rawson et al. | 128/736 |
| 4,270,529 A | 6/1981 | Muto | |
| 4,270,531 A | 6/1981 | Blachly et al. | 128/207.14 |
| 4,351,330 A | 9/1982 | Scarberry | 128/207.15 |
| 4,351,331 A | 9/1982 | Gereg | |
| 4,392,857 A | 7/1983 | Beran | |
| 4,425,911 A | 1/1984 | Luomanen et al. | 128/200.26 |
| 4,495,945 A | 1/1985 | Liegner | 128/200.26 |
| 4,502,478 A | 3/1985 | Lifton | 128/136 |
| 4,530,354 A | 7/1985 | Froilan | |
| 4,640,273 A | 2/1987 | Greene et al. | 128/136 |
| 4,676,240 A | 6/1987 | Gardy | 128/207.14 |
| 4,683,882 A | 8/1987 | Laird | |
| 4,699,616 A | 10/1987 | Nowak et al. | 604/180 |
| 4,744,358 A | 5/1988 | McGinnis | 128/207.17 |
| 4,774,944 A | 10/1988 | Mischinski | |
| 4,788,751 A | 12/1988 | Shely et al. | 24/16 PB |
| 4,791,941 A | 12/1988 | Schaefer | 128/861 |
| 4,944,313 A | 7/1990 | Katz et al. | 128/859 |

(Continued)

FOREIGN PATENT DOCUMENTS

| | | |
|---|---|---|
| WO | WO 01/58349 A1 | 8/2001 |
| WO | WO 01/62325 A1 | 8/2001 |
| WO | WO 01/91838 A1 | 12/2001 |

*Primary Examiner*—LoAn H. Thanh
(74) *Attorney, Agent, or Firm*—Elizabeth Arwine

(57) ABSTRACT

A securing device for a catheter that preferably includes a guard that covers a patient's upper or lower teeth and a latch mounted on the guard for releasably immobilizing a catheter with respect to the guard. The guard preferably includes (or is attached to) a wedge, which contacts the patient's molars to prevent the guard from shifting in the patient's mouth and assists in keeping the patients teeth apart.

18 Claims, 3 Drawing Sheets

U.S. PATENT DOCUMENTS

| | | | |
|---|---|---|---|
| 5,026,352 A | 6/1991 | Anderson | 604/178 |
| 5,069,206 A | 12/1991 | Crosbie | 128/207.17 |
| 5,123,410 A | 6/1992 | Greene et al. | 128/207.17 |
| 5,174,284 A | 12/1992 | Jackson | 128/200.26 |
| 5,193,544 A | 3/1993 | Jaffe | 128/634 |
| 5,205,281 A | 4/1993 | Buchanan | 128/207.14 |
| 5,282,464 A | 2/1994 | Brain | 128/207.15 |
| 5,305,742 A | 4/1994 | Styers et al. | |
| 5,318,017 A | 6/1994 | Ellison | 128/200.24 |
| 5,320,097 A | 6/1994 | Clemens et al. | |
| 5,355,874 A | 10/1994 | Bertram | 128/200.26 |
| 5,402,776 A | 4/1995 | Islava | |
| 5,413,095 A | 5/1995 | Weaver | 128/200.26 |
| 5,501,216 A | 3/1996 | Byrd | |
| 5,529,062 A | 6/1996 | Byrd | |
| 5,551,421 A | 9/1996 | Noureldin et al. | |
| 5,626,128 A * | 5/1997 | Bradley et al. | 128/200.26 |
| 5,655,519 A | 8/1997 | Alfery | 128/200.26 |
| 5,715,816 A | 2/1998 | Mainiero et al. | 128/633 |
| 5,746,202 A | 5/1998 | Pagan | 128/207.14 |
| 5,782,236 A | 7/1998 | Ess | 128/207.17 |
| 5,803,079 A | 9/1998 | Rogers et al. | 128/207.14 |
| 5,806,516 A | 9/1998 | Beattie | 128/207.17 |
| 5,829,430 A | 11/1998 | Islava | 128/200.26 |
| 5,894,840 A | 4/1999 | King | |
| 6,244,865 B1 | 6/2001 | Nelson et al. | 433/140 |
| 2002/0092526 A1 | 7/2002 | Bertoch et al. | |
| 2002/0095118 A1 | 7/2002 | Bertoch et al. | |

* cited by examiner

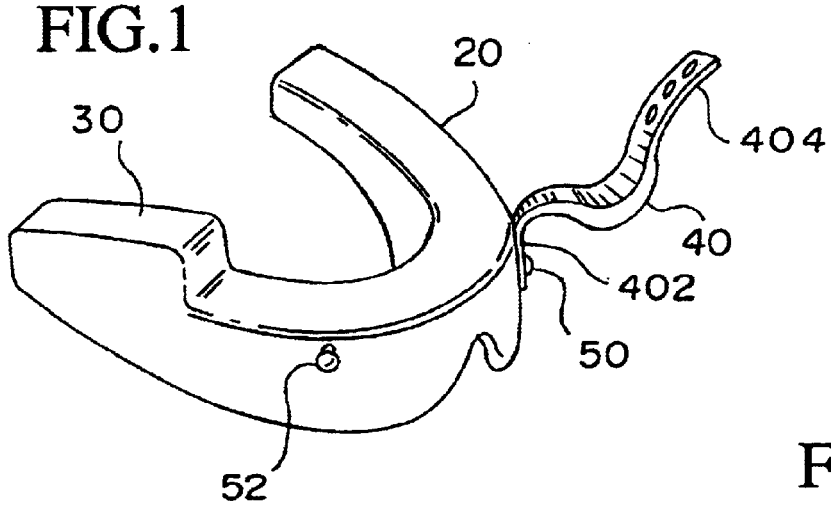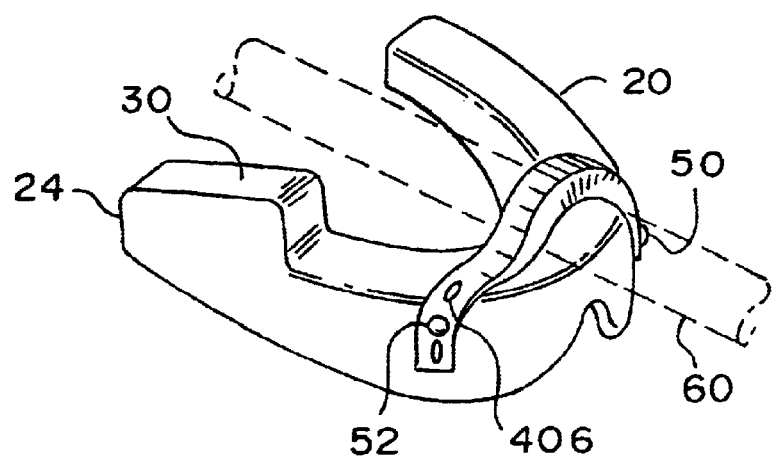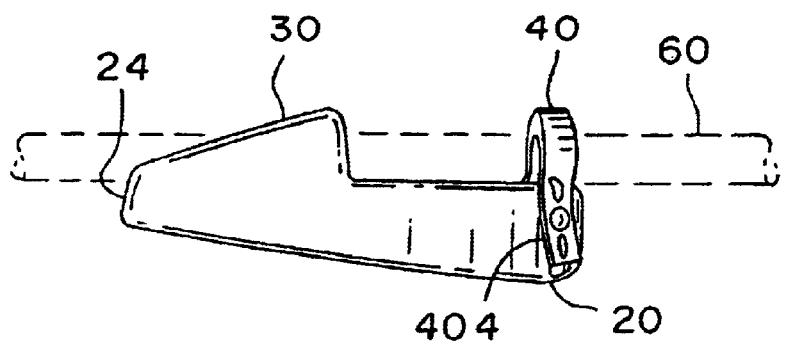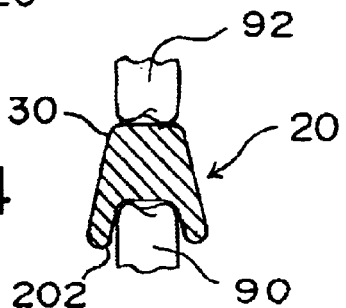

CATHETER SECURING DEVICE

This application claims the benefit of U.S. provisional Application Ser. No. 60/214,745, filed Jun. 29, 2000, which is hereby incorporated by reference.

I. FIELD OF THE INVENTION

This invention relates to a device for securing a catheter such as an endotracheal tube with respect to the patient's mouth while protecting the catheter against occlusion by the patient's teeth.

II. BACKGROUND OF THE INVENTION

Catheters are employed by medical personnel for many purposes such as providing for the passage of fluids, including gases, to and from the human body. In various medical procedures, it is common to introduce a catheter into a patient's airway through the mouth. One type of catheter is an endotracheal tube, which is adapted to be inserted through the oral cavity of a patient and into the trachea, for example, to provide for the supply of fluids to the body, for the monitoring of internal conditions in the body and for removal of secretions from within the body. Other examples of catheters include respiratory tubes for laryngeal masks, oral gastric tubes, and esophageal stethoscopes.

It is desirable to secure the catheter in place within the patient to prevent the catheter from being inadvertently mainstem intubated (advanced into the patient) or extubated (retracted (or removed) from the patient's mouth) after it has been properly positioned; however, it is difficult to properly secure catheters to a patient's face to prevent these events. Neck straps are effective for holding catheters, but the neck straps can often hinder jugular venous flow or impede line placement within the patient. Tapes and adhesives are ineffective routinely, because of the presence of facial hair, dirt, blood, debris, perspiration, excessive soft tissue or facial trauma.

Another problem is that the catheter is usually relatively easy to deform as it passes between the patient's teeth when inserted orally, it is desirable to prevent the lumen of the catheter from being occluded by a patient's teeth when the patient attempts to bite down. Occlusion of the catheter can lead to, for example, hypoxia, hypercarbia, and the syndrome known as negative pressure pulmonary edema. The various restraining approaches discussed above are ineffective in protecting against possible occlusion of the catheter.

Bite blocks can be effective in keeping a patient's jaw open and thus prevent the teeth from clamping down on the catheter. One problem with a bite block is that it is yet another piece of equipment that may be inserted into the patient's mouth along with other medical apparatuses including, for example, multiple hoses/tubes/catheters and pulse oximeter sensors. Another problem with some bit blocks that set loose within the oral cavity is that if the patient's mouth opens up wider than the bite block, the bite block may move from its position down into the patient's throat or airway. If this occurs, then the airway may become partially or completely blocked. In any event, someone will need to fish out the bite block with an instrument or hand while keeping the patient's mouth open.

A recurring problem during intubation is that a patient's teeth suffer dental trauma from being hit and/or jarred. This type of dental trauma results in the number one cause of claims against anesthesiologists. Thus, it is desirable to find a device capable of protecting a patient's teeth from dental trauma.

Notwithstanding the above devices, a need still exists for an apparatus to secure a catheter in place within the patient while also preventing the patient from occluding the inserted catheter and protecting the patient's teeth.

III. SUMMARY OF THE INVENTION

The present invention provides a securing device for a catheter that can easily immobilize the catheter with respect to a patient while preventing occlusion of the catheter by the patient's teeth and protecting the patient's teeth.

The present invention additionally provides a securing device for a catheter, which permits the vicinity of a patient's mouth to be easily cleaned.

According to one form of the present invention, a securing device for securing a catheter within a patient's mouth includes a guard shaped to fit over the teeth of a patient (or subject including human and animal) within the patient's mouth and a latch mounted on the guard for releasably holding the catheter.

In a preferred embodiment, the guard includes a recess on a first side thereof for receiving a first molar of the patient and a wedge on a second side thereof for contacting a second molar of the patient opposing the first molar. Contact between the recess, the wedge, and the molars prevents the securing device from shifting within the patient's mouth during use.

According to another form of the present invention, a method of securing a catheter within a patient's mouth includes covering a plurality of a patient's teeth with a guard, inserting the catheter into a patient's mouth, and securing the catheter to the guard.

According to one aspect of the invention, a device for securing a catheter within a mouth of a patient including a guard having an anterior region and two posterior regions, and a latch in communication with the guard; and wherein each of the posterior regions abuts the anterior region, and the posterior regions are spaced from each other. According to another aspect of the invention, the method for using the device includes covering a plurality of a patient's teeth with the guard disposed in the patient's mouth; inserting the catheter into the patient's mouth; and securing the catheter by clamping the catheter between the guard and the latch.

According to one aspect of the invention, a securing device includes means for protecting at least some teeth of a patient, means for maintaining a distance between the protected teeth and the opposing teeth, and means for holding a catheter against the teeth protecting means.

According to one aspect of the invention, a device for securing a catheter within a mouth of a patient includes a guard including a channel framed by two side walls and a wall connecting the side walls, a first post, and a second post, the guard having an anterior region and two posterior regions, a latch in communication with the first post of the guard, the latch engages the second post, and a wedge extending from the guard in one of the two posterior regions; and wherein the first post and the second post are spaced from each other in the anterior region.

An objective of the invention is to protect a patient's teeth during orotracheal intubation.

A further objective of the invention is to hold and maintain a catheter at a preselected depth within a patient.

A further objective of the invention is to allow easy adjustment of the depth of a catheter within a patient.

A yet further objective of the invention is to provide a rapid, simple, and effective means for securing a catheter without the requirement of other materials such as ties or tape.

Another objective of the invention is to prevent occlusion of a catheter and thus avoid, for example, hypoxia, hypercarbia and/or negative pressure pulmonary edema.

Another objective of the invention is to provide a compact, easy-to-use, lightweight apparatus, which can be either disposable or re-usable.

Another objective of the invention is to solve the above-stated problems of the prior art.

An advantage of the invention is that it efficiently and effectively secures a catheter in place and maintains that placement position.

A further advantage of the invention is that medical personnel may quickly and easily adjust the depth of a catheter traveling through a patient's oral cavity.

A further advantage of the invention is a compact and simple design.

A further advantage of the invention is the ease of securing catheters as compared to the prior art.

A yet further advantage of the invention is that once placed in the patient's mouth no part extends beyond the lips of the patient.

Further features and advantages of the present invention, as well as the structure and operation of various embodiments of the present invention, are described in detail below with reference to the accompanying drawings.

IV. BRIEF DESCRIPTION OF THE DRAWINGS

The present invention is described with reference to the accompanying drawings. In the drawings, like reference numbers indicate identical or functionally similar elements. The use of cross-hatching and shading within the drawings is not intended as limiting the type of materials that may be used to manufacture the invention.

FIG. 1 illustrates a perspective view from the top of a preferred embodiment of the invention with a latch in an open position.

FIG. 2 depicts a perspective view from the top of the embodiment of FIG. 1 with the latch in a closed position and a catheter shown in phantom.

FIG. 3 illustrates a side elevation of the embodiment of FIG. 1 with the latch in a closed position and a catheter shown in phantom.

FIG. 4 is a schematic cross-sectional view of the embodiment of FIG. 1 illustrating a portion of the securing device disposed between a patient's molars on the right side of the mouth.

V. DESCRIPTION OF PREFERRED EMBODIMENTS

A preferred embodiment of a securing device according to the present invention will be described with reference to FIGS. 1–10. The invention preferably includes a guard 20, a wedge 30, and a latch 40 as illustrated in FIGS. 1–10.

Figure 5:
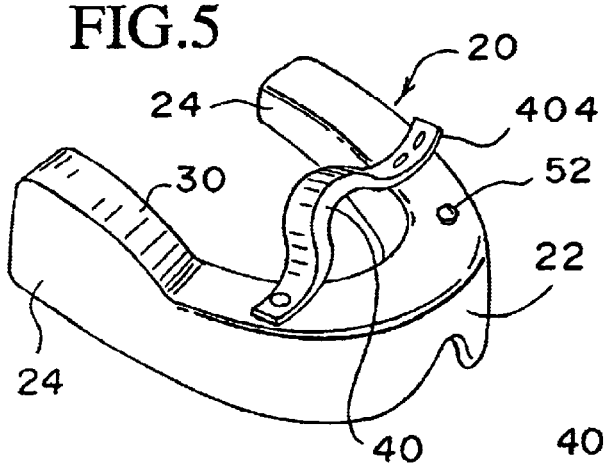
FIG. 5 illustrates a perspective view from the top of the invention with the latch in an open position.
Figure 6:
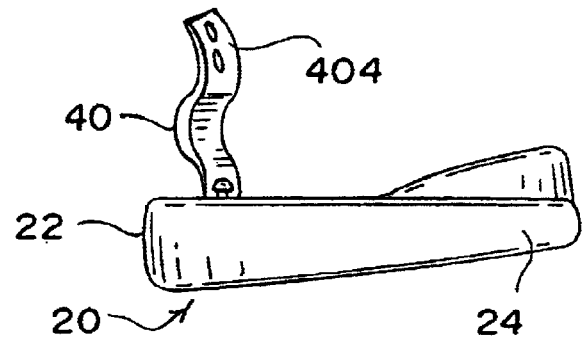
FIG. 6 depicts a side (opposite the wedge) view of the embodiment illustrated in FIG. 5 with the latch in an open position.
Figure 7:
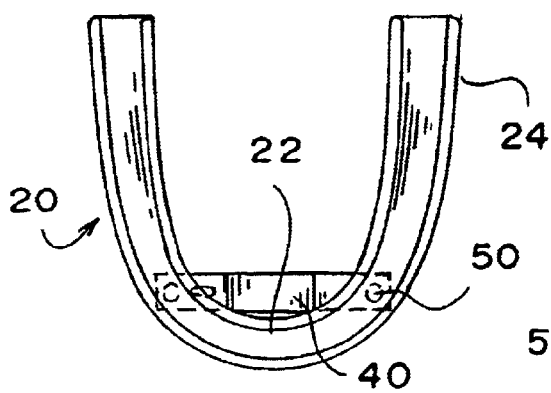
FIG. 7 illustrates a bottom view of the embodiment illustrated in FIG. 5.
Figure 8:
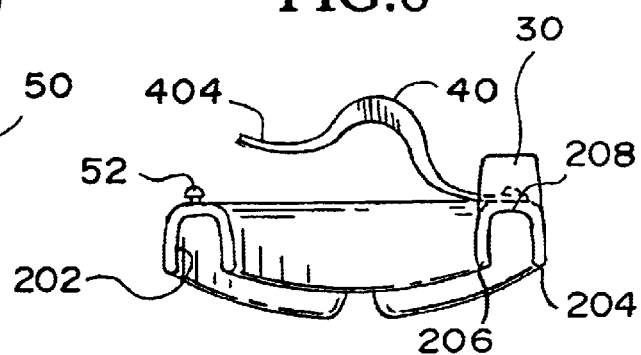
FIG. 8 depicts a rear view of the embodiment illustrated in FIG. 5 with the latch in an open position.

The guard (or teeth protecting means) 20 preferably is shaped to fit over at least a portion of the lower teeth of a patient and more preferably all of the lower teeth of the patient while not restraining the tongue. Alternatively, the guard 20 may be used to fit over the upper teeth of the patient. The guard 20 preferably is generally U-shaped as shown, for example, in FIGS. 1 and 5 with an anterior region 22 and two posterior regions 24. The posterior regions 24 preferably are formed to track the general shape of the patient's jaw. As illustrated in FIGS. 4 and 8, the guard 20 preferably has a generally U-shaped transverse cross-section so as to define a channel 202 extending over its entire length for shrouding or covering the lower teeth 90. The channel 202 preferably is framed by two side walls 204, 206 and a connecting wall (or ceiling/bottom) 208 as illustrated, for example, in FIG. 8. Alternatively, portions of one (or some or all) of the walls 204, 206, 208 may be removed while still accomplishing the objectives of the invention and obtaining the advantages of the invention. Although the Figures illustrate the guard 20 having an angled bottom relative to a horizontal plane, the guard 20 may instead have a horizontal bottom.

Figure 9:
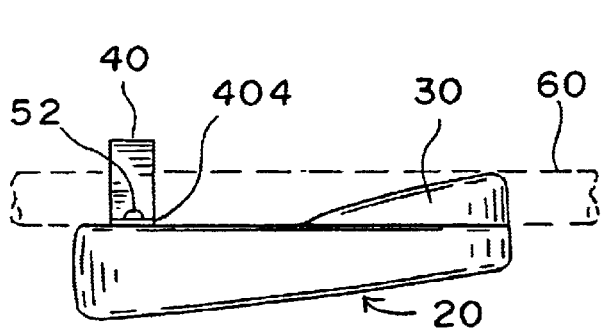
FIG. 9 illustrates another side view of the embodiment illustrated in FIG. 5 with the latch in a closed position and a catheter in phantom.
Figure 10:
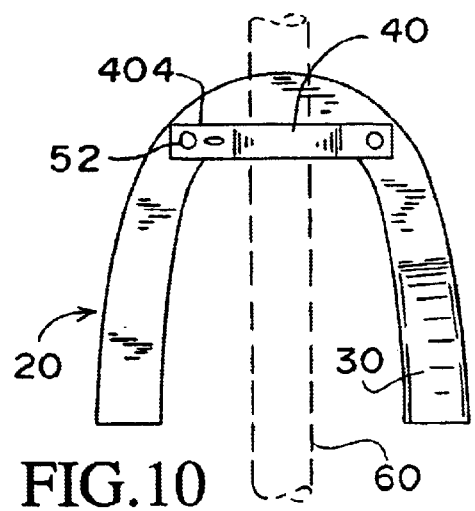
FIG. 10 depicts a top view of the embodiment illustrated in FIG. 5 with the latch in a closed position and a catheter in phantom.

A raised molar wedge (or bite block or distance maintaining means) 30 for contacting the upper molars of a patient's mouth preferably extends up from and/or is connected to one of the posterior regions 24 along the top surface of the guard 20 as illustrated, for example, in FIGS. 3 and 9, which respectively show two different exemplary orientations for the wedge 30. The height of the wedge 30 preferably is such that the top of the wedge 30 will snugly contact the lower surface of one or more of the patient's upper molars 92, as illustrated in FIG. 4, to space the opposing upper and lower molars from each other by a sufficient distance to prevent the patient from bringing his upper and lower incisors into contact with each other and any inserted catheter or instrument. The separation between the upper and lower incisors preferably is larger than the outer diameter of a catheter to be introduced into the patient's mouth so as to prevent occlusion of the catheter by the patient's teeth. To reduce the load applied to any one tooth, the top of the wedge 30 is preferably long enough to contact a plurality of the patient's molars at the same time. Thus, the wedge 30 assists in preventing the guard 20 from shifting in the patient's mouth. As illustrated in FIGS. 1–3 and 5–10, the wedge 30 is shown positioned on the portion of the guard 20 corresponding to the right side of a patient's mouth, but alternatively the wedge 30 may be installed on the opposite side or on both sides.

The latch (or holding means) 40 preferably is pivotally mounted with respect to the guard 20 for securing the catheter. The latch 40 preferably is a curved member mounted on the anterior region 22 of the guard 20. The latch 40 preferably includes a first end 402 which is rotatably mounted on a first peg (or post) 50 secured to the guard 20 and a second end 404 having a plurality of holes 406 formed therein. Preferably, each of the holes 406 detachably fit over a second peg (or post or hook) 52 secured to the guard 20 on the side opposite from the first peg 50 in the anterior region 22. Preferably, both the first peg 50 and the second peg 52 extend from the guard 20 and more preferably both the pegs 50, 52 are integrally formed with the guard 20. FIGS. 1 (on the front) and 5 (along the top) illustrate possible and exemplary placements for the first peg 50 and the second peg 52 in the anterior region 22.

FIG. 1 shows the latch 40 in an open position in which it is rotated to the side so as not to interfere with intubation, and FIGS. 2 and 3 show the latch 40 in a closed position to secure a catheter to the guard 20. When the second end 404 of the latch 40 is secured to the second peg 52, a catheter 60 (shown in phantom in FIGS. 2 and 3) can be clamped snugly between the guard 20 and the latch 40 to prevent the catheter 60 from being easily translated in its lengthwise and lateral directions with respect to the guard 20. The plurality of holes 406 on the second end 404 preferably enable the latch 40 to be used with different sized catheters 60. In addition to holding the catheter 60 in place with respect to the guard 20, the latch 40 preferably is sufficiently rigid to shield the catheter 60 from being occluded by the patient's lower and upper incisors and this rigidity provides a means for protecting the catheter from occlusion.

The dimensions and exact shape of the guard 20 can be varied in accordance with the shape of the mouth of the patient with whom the securing device is to be used. For example, the size and shape of the guard 20 may vary based on the size and age of the patient.

The guard 20, wedge 30 and pegs 50, 52 preferably are resilient, non-toxic material that may include at least one of the following materials: rubber or plastic such as rigid thermoplastic or polyurethane. Examples of possible thermoplastics include thermoplastic elastic polymers mixed with polycaprolactone and thermoplastic elastic polymers mixed with polycaprolactone and polyvinyl acetate. The thermoplastic elastic polymers may be, for example, ethylene/vinyl acetate copolymers. Preferably, if the guard 20 includes rubber, then the rubber has some resiliency. Other examples of materials that may be used for the guard 20 include those materials used to manufacture mouth guards commonly used for contact sports such as football. Furthermore, any material that is sufficiently resilient but yet soft such that the patient's teeth will be protected from dental trauma from use of this invention may be used for the guard 20 and the wedge 30. Additionally, the wedge 30 may be made with material similar to that of the guard 20 and even be integrally formed with the guard 20. The wedge 30 also may be a structure that includes a hollow portion to allow for some compression and provide further protection of the patient's upper teeth.

The latch 40 can be either flexible or rigid and may be made of a wide variety of materials, including materials that can be used for the guard 20. Preferably, the latch 40 will be sufficiently rigid to prevent vertical compression in response to the patient biting down. This rigidity will allow the latch 40 to maintain an arcuate shape above and on the sides of the catheter even when the latch 40 is contacted by a patient's upper incisors, thus preventing occlusion of the catheter.

A method for using the securing device is as follows. The guard 20 preferably is inserted into the mouth of a patient to be intubated over the patient's lower teeth such that one or more of the patient's upper right molars snugly contacting the wedge 30. FIG. 4 is a schematic transverse cross-sectional view of the securing device showing one of the patient's lower right molars 90 received in and snugly pressed within channel 202 in the guard 20 with one of the patient's upper right molars 92 snugly pressed against the top of the wedge 30. After the guard 20 is inserted, preferably the latch 40 is rotated to the side of the guard 20 where the first peg 50 is located, if necessary.

Preferably, intubation is then carried out in a conventional manner to position the catheter 60 at a desired depth and location in the patient's airway. During intubation, the guard 20 preferably protects the patient's lower teeth from dental trauma. After the catheter 60 has been properly positioned, the latch 40 preferably is placed around the catheter 60 and the second end 404 of the latch 40 preferably is secured to the second peg 52 to snugly hold the catheter 60 against the guard 20 without occluding the catheter 60. The catheter 60 preferably is now releasably immobilized against movement with respect to the patient.

If it is subsequently desired to adjust the position of the catheter 60, the latch 40 can be released by disconnecting the second end 404 of latch 40 from the second peg 52 to permit the catheter 60 to move with respect to the guard 20. The securing device is thus very easy to install and adjust.

Figure 11:
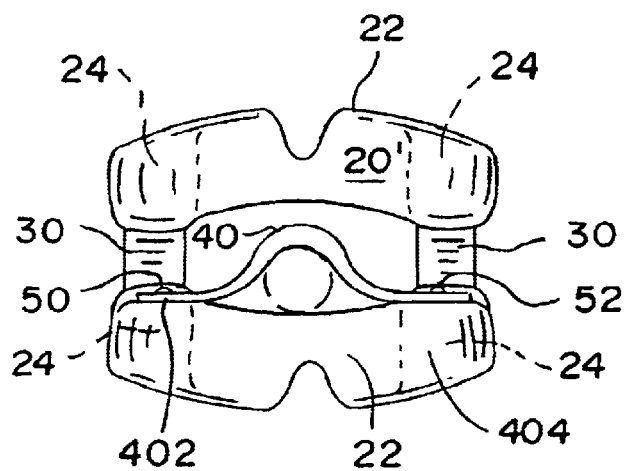
FIG. 11 illustrates a front view of an alternative embodiment of the invention and a catheter in phantom.
Figure 12:
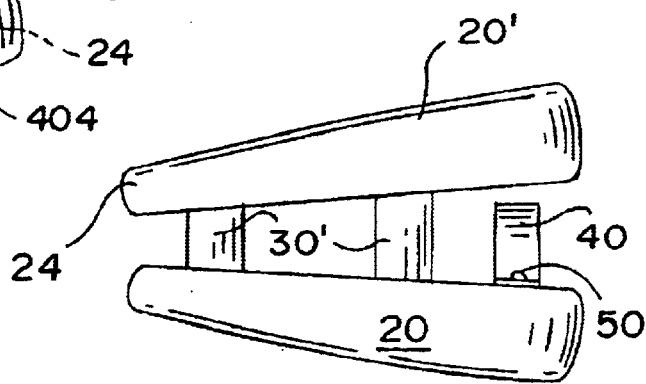
FIG. 12 depicts a side view of a modification to the alternative embodiment illustrated in FIG. 11.

An alternative embodiment is to have two guards 20, 20' joined by either one or two wedges 30 as illustrated in FIG. 11 (a two wedge example). The top guard 20' preferably does not include the latch 40 and pegs 50, 52 as illustrated. Also, as a result of the structure, the lower guard 20 may also not include the latch 40 and pegs 50, 52 (not shown). A modification to this alternative embodiment is to replace the illustrated wedges 30, 30 (FIG. 11) with columns 30', which preferably are fixed height, as illustrated in FIG. 12. As with the dual wedge alternative embodiment, this embodiment also may remove the latch 40 and pegs 50, 52 from either the top guard 20', the bottom guard 20, or both. The top guard 20' may alternatively have a bottom wall 208 and a front wall 204 with a "L" cross-section and no rear wall 206 to allow easier insertion of the device into a patient's mouth.

Figure 15:
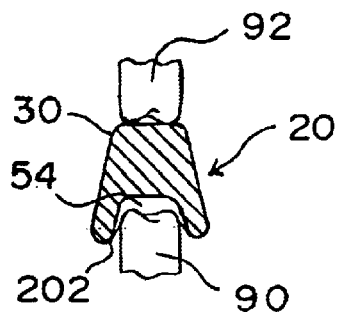
FIG. 15 is a schematic cross-sectional view of an alternative embodiment of the invention illustrating a portion of the securing device disposed between a patient's molars on the right side of the mouth.

As illustrated in FIG. 15, another alternative embodiment is to fill the channel 202 within the guard with a foam or other similar soft material 54 to provide a better fit to the patient's teeth. This alternative embodiment will also preferably provide additional cushion to any jarring that might occur during intubation or insertion/removal of other medical devices and instruments through the oral cavity. The foam preferably will be a closed cell, foamed polyolefin such as Minicel L200 from Voitek Division of Sekisui America Corp. of Lawrence, Mass. or a similar material.

Figure 13A:
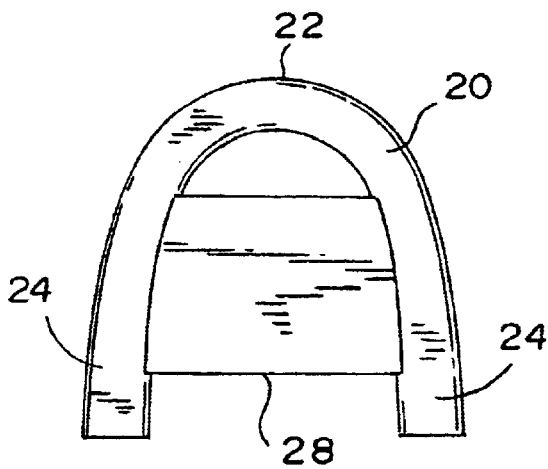
FIG. 13(a) illustrates a top view of an alternative embodiment of the invention.
Figure 13B:
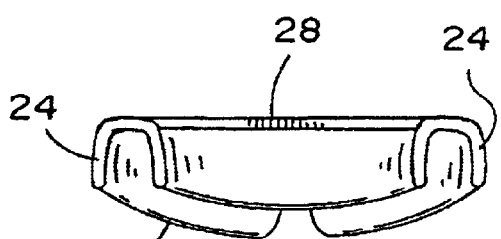
FIG. 13(b) illustrates a rear view of the alternative embodiment in FIG. 13(a).

Another alternative embodiment is illustrated in FIGS. 13(a) and (b). The guard 20 may include a member (or shield) 28 extending between the posterior regions 24, 24 for covering the patient's tongue and protecting it against trauma during intubation and/or the medical procedure being performed. Preferably, the member 28 will be flush with connecting wall 208 as illustrated in FIG. 13(b). The member 28 may alternatively cover the area created within the oral cavity as framed by the guard 20, i.e., creating a tongue cavity ceiling. Preferably, the member 28 will extend from the top of the guard 20 such that a cavity is formed below the member 28 for the tongue. In addition to protecting the tongue, the member 28 will restrain the tongue from getting in the way of the intubation or other medical procedure.

Another alternative embodiment is to have the first peg 50 integrally formed with the latch 40. In this embodiment, the first peg 50 preferably will have a ball and socket fit with a hole in the anterior region 22 of the guard 20. Any type of engagement that will allow the latch 40 to rotate (or move) about the engagement point of the first peg 50 with the guard 20 may replace the ball and socket fit.

Figure 14:
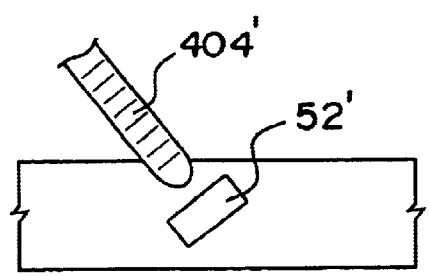
FIG. 14 depicts an enlarged view of an alternative connection between the guard and the latch of the invention.

Another alternative embodiment is to replace the second peg 52 with a locking head 52' and the second latch end 404 with a serrated strap 404' as illustrated in FIG. 14. The locking head 52' preferably includes a locking tang for engaging the serrations in the serrated strap 404'. Preferably, the locking tang allows for insertion and removal of the serrated strap 404' to allow for adjustment of the catheter relative to the invention.

While the illustrated securing device was described as fitting over a patient's lower teeth, it is instead possible for it to be mounted over the patient's upper teeth.

The securing device, the preferred illustrated embodiment and the various alternative embodiments, preferably does not have any portion, which extends to the exterior of a patient's mouth during use, so it is easy to keep the vicinity of the patient's mouth clear of bodily fluids or other types of contamination. The securing device is immobilized within the patient's mouth, so it is unnecessary to employ straps or tape on the exterior of the patient's head, which can cause discomfort to the patient and interfere with cleaning of the patient. The securing device also permits ready access to the interior of the patient's mouth after intubation so that the condition of the patient's mouth can be observed and the accumulation of fluids within the patient's mouth can be prevented. Furthermore, the securing device leaves ample room within the oral cavity for additional instruments to be inserted.

The preferred and alternative embodiments described above may be combined in a variety of ways with each other.

Although the present invention has been described in terms of particular preferred and alternative embodiments, it is not limited to those embodiments. Alternative embodiments, examples, and modifications which would still be encompassed by the invention may be made by those skilled in the art, particularly in light of the foregoing teachings.

Those skilled in the art will appreciate that various adaptations and modifications of the preferred and alternative embodiments described above can be configured without departing from the scope and spirit of the invention. Therefore, it is to be understood that, within the scope of the appended claims, the invention may be practiced other than as specifically described herein.

What is claimed is:

1. A device for securing a catheter within a mouth of a patient comprising:
    a guard having
        an anterior region, and
        two posterior regions, and
    a latch in communication with said guard, and
    a wedge connected to said guard and extending from one of said posterior regions; and
    wherein each of said posterior regions abuts said anterior region, and said posterior regions are spaced from each other.

2. The device as claimed in claim 1, wherein said latch is mounted on said guard for rotation between an open position and a closed position.

3. A device for securing a catheter within a mouth of a patient comprising:
    a guard having
        an anterior region, and
        two posterior regions, and
    a latch in communication with said guard said latch has a first end rotatably connected to said guard and a second end detachably engagable with said guard; and
    wherein each of said posterior regions abuts said anterior region, and said posterior regions are spaced from each other.

4. The device according to claim 1, wherein said latch includes an end with a ball, and said guard having a socket for receiving said ball of said latch.

5. The device according to claim 1, wherein said guard includes a channel framed by two side walls and a wall connecting said two side walls such that said walls are in each of said anterior and two posterior regions.

6. The device for securing a catheter within a mouth of a patient comprising:
    a guard having
        an anterior region,
        two posterior regions,
        a channel framed by two side walls and a wall connecting said two side walls such that said walls are in each of said anterior and two posterior regions, and
        a soft material lining at least said connecting wall within the channel,
    a latch in communication with said guard, and
    a wedge connected to said guard; and
    wherein each of said posterior regions abuts said anterior region, and said posterior regions are spaced from each other.

7. The device according to claim 1, further comprising a shield connecting said two posterior regions of said guard together.

8. A device for securing a catheter within a mouth of a patient comprising:
    a guard having
        an anterior region, and
        two posterior regions, wherein each of said posterior regions abuts said anterior region, and said posterior regions are spaced from each other,
    a latch in communication with said guard, and a wedge extending from said guard, and
    wherein said guard includes a first post and a second post, said first post is in communication with said latch.

9. The device according to claim 8, wherein said latch engages said second post.

10. The device according to claim 8, wherein said first post and said second post are spaced in said anterior region.

11. The device according to claim 8, wherein said latch includes an arcuate portion.

12. The device according to claim 11, wherein said wedge extends from said guard in one of said two posterior regions.

13. The device according to claim 1, further comprising: a second guard having an anterior region and two posterior regions, said first wedge connecting said guard and said second guard together in one of said posterior regions, and a second wedge connecting said guard and said second guard together in the other of said posterior regions.

14. A method of securing a catheter within a patient's mouth using the device of claim 1 comprising:
    covering a plurality of a patient's teeth with the guard disposed in the patient's mouth;

inserting the catheter into the patient's mouth; and securing the catheter by clamping the catheter between the guard and the latch.

15. A securing device comprising:

means for protecting at least some teeth of a patient, means for maintaining a distance between the protected teeth and the opposing teeth, and means for holding a catheter against said teeth protecting means.

16. The securing device according to claim 15, wherein said holding means includes means for protecting the catheter from occlusion.

17. A device for securing a catheter within a mouth of a patient comprising:

a guard including
  a channel framed by two side walls and a wall connecting said side walls,
  a first post, and
  a second post, said guard having an anterior region and two posterior regions, a latch in communication with said first post of said guard, said latch engages said second post, and a wedge extending from said guard in one of said two posterior regions; and wherein said first post and said second post are spaced from each other in said anterior region.

18. The device according to claim 17, wherein said latch includes an end that engages said second post, when said end engages said second post, said latch clamps the catheter in place against said guard, when said end engages said second post, said latch prevents closure of a jaw of the patient, and said wedge prevents closure of the jaw of the patient.

* * * * *

UNITED STATES PATENT AND TRADEMARK OFFICE
CERTIFICATE OF CORRECTION

PATENT NO. : 6,890,322 B2
APPLICATION NO. : 09/894880
DATED : May 10, 2005
INVENTOR(S) : Bertoch et al.

Page 1 of 1

It is certified that error appears in the above-identified patent and that said Letters Patent is hereby corrected as shown below:

Column 8,
line 19, claim 6, change "A" to --The--

Signed and Sealed this

Twenty-second Day of January, 2008

JON W. DUDAS
*Director of the United States Patent and Trademark Office*